(12) United States Patent
Li

(10) Patent No.: US 12,207,816 B2
(45) Date of Patent: Jan. 28, 2025

(54) ANVIL ASSEMBLY WITH REDUCED DEFLECTION

(71) Applicant: Covidien LP, Mansfield, MA (US)

(72) Inventor: Xijia Li, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/278,716

(22) PCT Filed: Feb. 25, 2021

(86) PCT No.: PCT/CN2021/077893
§ 371 (c)(1),
(2) Date: Aug. 24, 2023

(87) PCT Pub. No.: WO2022/178758
PCT Pub. Date: Sep. 1, 2022

(65) Prior Publication Data
US 2024/0138832 A1 May 2, 2024

(51) Int. Cl.
*A61B 17/072* (2006.01)

(52) U.S. Cl.
CPC .............. *A61B 17/072* (2013.01); *A61B 2017/07221* (2013.01); *A61B 2017/07257* (2013.01); *A61B 2017/07278* (2013.01)

(58) Field of Classification Search
CPC .............................. A61B 17/072; A61B 17/32
See application file for complete search history.

(56) References Cited

U.S. PATENT DOCUMENTS

| | | |
|---|---|---|
| 1,158,111 A | 10/1915 | Ahlheim |
| 2,891,250 A | 6/1959 | Hirata |
| 3,080,564 A | 3/1963 | Strekopitov et al. |
| 3,252,643 A | 5/1966 | Strekopov et al. |
| 3,269,630 A | 8/1966 | Fleischer |
| 3,275,211 A | 9/1966 | Hirsch et al. |
| 3,315,863 A | 4/1967 | O'Dea |
| 3,494,533 A | 2/1970 | Green et al. |
| 3,589,589 A | 6/1971 | Akopov |
| 3,692,224 A | 9/1972 | Astafiev et al. |
| 3,795,034 A | 3/1974 | Strekopytov et al. |
| 3,822,818 A | 7/1974 | Strekopytov et al. |

(Continued)

FOREIGN PATENT DOCUMENTS

| | | |
|---|---|---|
| CN | 101031246 A | 9/2007 |
| CN | 103860230 B | 7/2016 |

(Continued)

OTHER PUBLICATIONS

International Search Report for Application No. PCT/CN2021/077893 dated Dec. 1, 2021.

(Continued)

*Primary Examiner* — Nathaniel C Chukwurah

(57) ABSTRACT

A surgical stapling device includes an end effector having a cartridge assembly, and anvil assembly that is supported adjacent the anvil assembly in cantilevered fashion. The end effector of the stapling device includes a pusher that is configured to compensate for deflection of the anvil assembly and provide uniform staple formation along the length of the anvil assembly. The pusher is also configured to minimize firing forces required to fire staples from the cartridge assembly and cut tissue.

20 Claims, 6 Drawing Sheets

(56) References Cited

U.S. PATENT DOCUMENTS

| | | | |
|---|---|---|---|
| 3,935,981 A | 2/1976 | Akopov et al. |
| 3,949,923 A | 4/1976 | Akopov et al. |
| 4,047,654 A | 9/1977 | Alvarado |
| 4,216,891 A | 8/1980 | Behlke |
| 4,244,372 A | 1/1981 | Kapitanov et al. |
| 4,296,881 A | 10/1981 | Lee |
| 4,305,539 A | 12/1981 | Korolkov et al. |
| 4,354,628 A | 10/1982 | Green |
| 4,378,901 A | 4/1983 | Akopov et al. |
| 4,383,634 A | 5/1983 | Green |
| 4,402,444 A | 9/1983 | Green |
| 4,415,112 A | 11/1983 | Green |
| D273,513 S | 4/1984 | Spreckelmeier |
| 4,442,964 A | 4/1984 | Becht |
| 4,470,533 A | 9/1984 | Schuler |
| 4,475,679 A | 10/1984 | Fleury, Jr. |
| 4,485,811 A | 12/1984 | Chernousov et al. |
| 4,506,670 A | 3/1985 | Crossley |
| 4,506,671 A | 3/1985 | Green |
| 4,508,253 A | 4/1985 | Green |
| 4,522,327 A | 6/1985 | Korthoff et al. |
| 4,527,724 A | 7/1985 | Chow et al. |
| 4,530,453 A | 7/1985 | Green |
| 4,550,870 A | 11/1985 | Krumme et al. |
| 4,566,620 A | 1/1986 | Green et al. |
| 4,568,009 A | 2/1986 | Green |
| 4,573,622 A | 3/1986 | Green et al. |
| 4,580,712 A | 4/1986 | Green |
| 4,585,153 A | 4/1986 | Failla et al. |
| 4,589,582 A | 5/1986 | Bilotti |
| 4,602,634 A | 7/1986 | Barkley |
| 4,605,001 A | 8/1986 | Rothfuss et al. |
| 4,605,004 A | 8/1986 | Di Giovanni et al. |
| 4,606,344 A | 8/1986 | Di Giovanni |
| 4,606,345 A | 8/1986 | Dorband et al. |
| 4,607,636 A | 8/1986 | Kula et al. |
| 4,612,933 A | 9/1986 | Brinkerhoff et al. |
| 4,617,928 A | 10/1986 | Alfranca |
| 4,632,290 A | 12/1986 | Green et al. |
| 4,665,916 A | 5/1987 | Green |
| 4,684,051 A | 8/1987 | Akopov et al. |
| 4,714,187 A | 12/1987 | Green |
| 4,715,520 A | 12/1987 | Roehr, Jr. et al. |
| 4,728,020 A | 3/1988 | Green et al. |
| 4,767,044 A | 8/1988 | Green |
| 4,788,978 A | 12/1988 | Strekopytov et al. |
| 4,802,614 A | 2/1989 | Green et al. |
| 4,805,823 A | 2/1989 | Rothfuss |
| 4,819,853 A | 4/1989 | Green |
| 4,848,637 A | 7/1989 | Pruitt |
| 4,869,414 A | 9/1989 | Green et al. |
| 4,881,544 A | 11/1989 | Green et al. |
| 4,881,545 A | 11/1989 | Isaacs et al. |
| 4,915,100 A | 4/1990 | Green |
| 4,930,503 A | 6/1990 | Pruitt |
| 4,938,408 A | 7/1990 | Bedi et al. |
| 4,941,623 A | 7/1990 | Pruitt |
| 4,951,861 A | 8/1990 | Schulze et al. |
| 4,964,559 A | 10/1990 | Deniega et al. |
| 5,005,754 A | 4/1991 | Van Overloop |
| 5,018,657 A | 5/1991 | Pedlick et al. |
| 5,071,052 A | 12/1991 | Rodak et al. |
| 5,100,042 A | 3/1992 | Gravener et al. |
| 5,116,349 A | 5/1992 | Aranyi |
| 5,137,198 A | 8/1992 | Nobis et al. |
| 5,172,845 A | 12/1992 | Tejeiro |
| 5,190,203 A | 3/1993 | Rodak |
| 5,219,111 A | 6/1993 | Bilotti et al. |
| 5,240,163 A | 8/1993 | Stein et al. |
| 5,344,060 A | 9/1994 | Gravener et al. |
| 5,368,599 A | 11/1994 | Hirsch et al. |
| 5,405,073 A | 4/1995 | Porter |
| 5,413,267 A | 5/1995 | Solyntjes et al. |
| 5,439,155 A | 8/1995 | Viola |
| 5,452,836 A | 9/1995 | Huitema et al. |
| 5,458,279 A | 10/1995 | Plyley |
| 5,462,215 A | 10/1995 | Viola et al. |
| 5,464,144 A | 11/1995 | Guy et al. |
| 5,465,894 A | 11/1995 | Clark et al. |
| 5,470,006 A | 11/1995 | Rodak |
| 5,470,008 A | 11/1995 | Rodak |
| 5,470,009 A | 11/1995 | Rodak |
| 5,497,934 A | 3/1996 | Brady et al. |
| 5,503,320 A | 4/1996 | Webster et al. |
| 5,509,596 A | 4/1996 | Green et al. |
| 5,542,594 A | 8/1996 | McKean et al. |
| 5,547,117 A | 8/1996 | Hamblin et al. |
| 5,558,266 A | 9/1996 | Green et al. |
| 5,571,285 A | 11/1996 | Chow et al. |
| 5,579,978 A | 12/1996 | Green et al. |
| 5,580,067 A | 12/1996 | Hamblin et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,615,820 A | 4/1997 | Viola |
| 5,641,111 A | 6/1997 | Ahrens et al. |
| 5,678,748 A | 10/1997 | Plyley et al. |
| 5,697,543 A | 12/1997 | Burdorff |
| 5,706,997 A | 1/1998 | Green et al. |
| 5,706,998 A | 1/1998 | Plyley et al. |
| 5,732,871 A | 3/1998 | Clark et al. |
| 5,735,445 A | 4/1998 | Vidal et al. |
| 5,794,834 A | 8/1998 | Hamblin et al. |
| 5,810,240 A | 9/1998 | Robertson |
| 5,855,311 A | 1/1999 | Hamblin et al. |
| 5,878,937 A | 3/1999 | Green et al. |
| 5,893,506 A | 4/1999 | Powell |
| 5,894,979 A | 4/1999 | Powell |
| 5,964,394 A | 10/1999 | Robertson |
| 6,045,560 A | 4/2000 | McKean et al. |
| 6,638,285 B2 | 10/2003 | Gabbay |
| 6,805,273 B2 * | 10/2004 | Bilotti | A61B 17/115 227/176.1 |
| 6,817,508 B1 | 11/2004 | Racenet et al. |
| 6,988,650 B2 * | 1/2006 | Schwemberger | A61B 17/072 227/176.1 |
| 7,070,083 B2 | 7/2006 | Jankowski |
| 7,134,587 B2 * | 11/2006 | Schwemberger | A61B 17/072 227/176.1 |
| 7,147,139 B2 | 12/2006 | Schwemberger et al. |
| 7,147,140 B2 * | 12/2006 | Wukusick | A61B 17/072 227/176.1 |
| 7,204,404 B2 * | 4/2007 | Nguyen | A61B 17/072 227/176.1 |
| 7,207,472 B2 * | 4/2007 | Wukusick | A61B 17/072 227/181.1 |
| 7,210,609 B2 | 5/2007 | Leiboff et al. |
| 7,237,708 B1 | 7/2007 | Guy et al. |
| 7,275,674 B2 | 10/2007 | Racenet et al. |
| RE40,237 E | 4/2008 | Bilotti et al. |
| 7,407,076 B2 | 8/2008 | Racenet et al. |
| 7,431,190 B2 | 10/2008 | Hoffman |
| 7,522,854 B2 | 4/2009 | Kinouchi et al. |
| 7,549,563 B2 | 6/2009 | Mather et al. |
| 7,568,605 B2 * | 8/2009 | Kruszynski | A61B 17/072 227/19 |
| 7,641,092 B2 | 1/2010 | Kruszynski et al. |
| 7,717,312 B2 | 5/2010 | Beetel |
| 7,731,073 B2 | 6/2010 | Wixey et al. |
| 7,735,704 B2 * | 6/2010 | Bilotti | A61B 17/072 227/176.1 |
| 7,766,207 B2 | 8/2010 | Mather et al. |
| 7,810,690 B2 | 10/2010 | Bilotti et al. |
| 7,828,188 B2 | 11/2010 | Jankowski |
| 7,886,953 B2 * | 2/2011 | Schwemberger | A61B 17/072 227/19 |
| 8,016,176 B2 | 9/2011 | Kasvikis et al. |
| 8,029,520 B2 | 10/2011 | Korvick et al. |
| 8,033,439 B2 | 10/2011 | Racenet et al. |
| 8,070,038 B2 | 12/2011 | Kostrzewski |
| 8,231,041 B2 | 7/2012 | Marczyk et al. |
| 8,292,904 B2 | 10/2012 | Popovic et al. |

(56) References Cited

U.S. PATENT DOCUMENTS

| | | | |
|---|---|---|---|
| 8,328,064 B2 | 12/2012 | Racenet et al. | |
| 8,360,296 B2 | 1/2013 | Zingman | |
| 8,424,738 B2 | 4/2013 | Kasvikis | |
| 8,499,994 B2 | 8/2013 | D'Arcangelo | |
| 8,596,515 B2 | 12/2013 | Okoniewski | |
| 8,627,994 B2 | 1/2014 | Zemlok et al. | |
| 8,646,673 B2 | 2/2014 | Bilotti et al. | |
| 8,757,467 B2 | 6/2014 | Racenet et al. | |
| 8,936,185 B2 | 1/2015 | Racenet et al. | |
| 8,955,732 B2 | 2/2015 | Zemlok et al. | |
| 8,967,446 B2 | 3/2015 | Beardsley et al. | |
| 9,022,273 B1 | 5/2015 | Marczyk et al. | |
| 9,125,651 B2 * | 9/2015 | Mandakolathur Vasudevan | A61B 17/072 |
| 9,192,382 B2 | 11/2015 | Kostrzewski | |
| 9,192,387 B1 | 11/2015 | Holsten et al. | |
| 9,480,474 B2 | 11/2016 | Ji et al. | |
| 9,566,066 B2 | 2/2017 | Kasvikis | |
| 9,579,102 B2 | 2/2017 | Holsten et al. | |
| 9,655,619 B2 | 5/2017 | Zhang et al. | |
| 9,662,111 B2 | 5/2017 | Holsten et al. | |
| 9,668,736 B2 | 6/2017 | Holsten et al. | |
| 9,675,349 B2 | 6/2017 | Holsten et al. | |
| 9,675,350 B2 | 6/2017 | Holsten et al. | |
| 9,675,356 B2 | 6/2017 | Racenet et al. | |
| 9,814,460 B2 | 11/2017 | Kimsey et al. | |
| 9,888,923 B2 | 2/2018 | Chen et al. | |
| 9,962,159 B2 | 5/2018 | Heinrich et al. | |
| 10,004,504 B2 | 6/2018 | Bryant | |
| 10,085,754 B2 | 10/2018 | Sniffin et al. | |
| 10,194,913 B2 | 2/2019 | Nalagatla et al. | |
| 2004/0164123 A1 | 8/2004 | Racenet et al. | |
| 2005/0247752 A1 | 11/2005 | Kelly et al. | |
| 2005/0247753 A1 * | 11/2005 | Kelly | A61B 17/072 227/176.1 |
| 2006/0163312 A1 | 7/2006 | Viola et al. | |
| 2007/0187456 A1 | 8/2007 | Viola et al. | |
| 2010/0048988 A1 | 2/2010 | Pastorelli et al. | |
| 2013/0206813 A1 | 8/2013 | Nalagatla | |
| 2016/0249914 A1 | 9/2016 | Zhang et al. | |
| 2016/0249923 A1 | 9/2016 | Hodgkinson et al. | |
| 2016/0270784 A1 | 9/2016 | Wheeler et al. | |
| 2016/0270790 A1 | 9/2016 | Jankowski | |
| 2016/0270793 A1 | 9/2016 | Carter et al. | |
| 2016/0278779 A1 | 9/2016 | Jankowski | |
| 2017/0014134 A1 | 1/2017 | Chen et al. | |
| 2017/0027571 A1 | 2/2017 | Nalagatla et al. | |
| 2017/0027572 A1 | 2/2017 | Nalagatla et al. | |
| 2017/0027573 A1 | 2/2017 | Nalagatla et al. | |
| 2017/0027574 A1 | 2/2017 | Nalagatla et al. | |
| 2017/0128149 A1 | 5/2017 | Heinrich et al. | |
| 2017/0238923 A1 | 8/2017 | Holsten et al. | |
| 2017/0238924 A1 | 8/2017 | Holsten et al. | |
| 2017/0265861 A1 | 9/2017 | Holsten et al. | |
| 2018/0008261 A1 | 1/2018 | Racenet et al. | |
| 2018/0049739 A1 | 2/2018 | Kasvikis | |
| 2018/0153544 A1 * | 6/2018 | Maddur Shankarsetty | A61B 90/90 |
| 2018/0221024 A1 | 8/2018 | Heinrich et al. | |

FOREIGN PATENT DOCUMENTS

| | | |
|---|---|---|
| CN | 104107077 B | 8/2016 |
| CN | 107928733 A | 4/2018 |
| CN | 110381851 A | 10/2019 |
| WO | 2021022407 A1 | 2/2021 |

OTHER PUBLICATIONS

Written Opinion for Application No. PCT/CN2021/077893 dated Dec. 1, 2021.

* cited by examiner

ANVIL ASSEMBLY WITH REDUCED DEFLECTION

FIELD

The present technology is generally related to surgical stapling devices and, more particularly, to surgical stapling devices that have an anvil assembly that is supported on the stapling device in cantilevered fashion.

BACKGROUND

Surgical stapling devices are commonly used during a variety of surgical procedures to expedite dissection and suturing of tissue and minimize trauma to a patient. Typically, the stapling devices include an end effector that includes a cartridge assembly and an anvil assembly. The cartridge assembly and the anvil assembly are movable in relation to each other between open and clamped positions to clamp tissue therebetween. When the tissue is clamped between the cartridge and anvil assemblies, the stapling device can be fired to eject staples from the cartridge assembly into a staple forming surface of the anvil assembly to suture the tissue. The stapling devices often include a knife assembly that includes a cutting blade that is advanced from within the cartridge assembly into the anvil assembly to cut the tissue clamped between the cartridge and anvil assemblies.

Surgical stapling devices are available in a variety of types for performing a variety of different surgical procedures. One type of stapling device includes a U-shaped end effector that has a body having a first transverse portion, a second transverse portion, and a longitudinal portion interconnecting the first transverse portion and the second transverse portion. Each of the first and second end portions has a first end coupled to the longitudinal portion and a second end. The cartridge assembly is supported adjacent the second transverse portion and is movable towards the first transverse portion to move the anvil and cartridge assemblies into juxtaposed alignment. The anvil assembly is supported on the first transverse portion which extends from the longitudinal portion in cantilevered fashion.

During a surgical procedure, when the anvil and cartridge assemblies are moved into juxtaposed alignment and subsequently when the staples and the cutting blade are driven into the anvil assembly, the second end of the first transverse portion supporting the anvil assembly tends to bend or deflect distally away from the cartridge assembly such that a gap defined between the anvil and cartridge assemblies changes along the length of the anvil assembly. This may result in nonuniform staple formation.

A continuing need exists in the art for an end effector that can compensate for distal deflection of the second end of the anvil assembly during cutting of tissue.

SUMMARY

This disclosure is directed to a surgical stapling device that includes an end effector having a cartridge assembly and anvil assembly that is supported adjacent the anvil assembly in cantilevered fashion. The end effector of the stapling device includes a pusher that is configured to compensate for deflection of the anvil assembly and provide uniform staple formation along the length of the anvil assembly. The pusher is also configured to minimize firing forces required to fire staples from the cartridge assembly and cut tissue.

Aspects of this disclosure are directed to an end effector that includes a frame, an anvil plate, and a cartridge assembly. The frame has a U-shaped configuration and includes a first transverse portion, a second transverse portion, and a longitudinal portion interconnecting the first transverse portion and the second transverse portion. The longitudinal portion defines a longitudinal axis. The first transverse portion is spaced from the second transverse portion to define a recess. The first transverse portion is supported in cantilevered fashion on the longitudinal portion and has a first end coupled to the longitudinal portion of the frame and a second end spaced from the longitudinal portion of the frame. The anvil plate is supported on the first transverse portion of the frame and defines an axis that is substantially perpendicular to the longitudinal axis of the longitudinal portion of the frame. The cartridge assembly is supported in the recess defined between the first and second transverse portions of the frame and is movable in relation to the anvil plate between spaced and clamped positions. The cartridge assembly includes a cartridge body, staples, and a pusher that is movable within the cartridge body from a retracted position to an advanced position. The cartridge body defines a plurality of staple receiving slots that receives the staples. The pusher includes a base member and a plurality of fingers. Each of the plurality of fingers extends distally from the base member into one of the staple receiving slots and has a distal portion supporting one of the staples. The pusher is movable within the cartridge body from a retracted position towards an advanced position to eject the staples from the staple receiving slots. The distal portions of the plurality of fingers are aligned along an axis "P1" and the anvil shaft defines an axis "P2", wherein the axis "P1" defines an angle of from about 2 degrees to about 10 degrees with the axis "P2" when the pusher is in a retracted position, and the axis "P1" is substantially parallel to the axis "P2" when the staples are ejected into the anvil plate.

Other aspects of this disclosure are directed to surgical stapling device including a handle assembly, an elongate body, and an end effector. The elongate body has a proximal portion coupled to the handle assembly and a distal portion. The end effector is coupled to the distal portion of the elongate body and includes a frame, an anvil plate, and a cartridge assembly. The frame has a U-shaped configuration and includes a first transverse portion, a second transverse portion, and a longitudinal portion interconnecting the first transverse portion and the second transverse portion. The longitudinal portion defines a longitudinal axis. The first transverse portion is spaced from the second transverse portion to define a recess. The first transverse portion of the frame is supported in cantilevered fashion on the longitudinal portion of the frame and has a first end coupled to the longitudinal portion and a second end spaced from the longitudinal portion. The anvil plate is supported on the first transverse portion of the frame and defines an axis that is substantially perpendicular to the longitudinal axis of the longitudinal portion of the frame. The cartridge assembly is supported in the recess defined between the first and second transverse portions of the frame. The cartridge assembly is movable in relation to the anvil plate between spaced and clamped positions. The cartridge assembly includes a cartridge body, staples, and a pusher that is movable within the cartridge body from a retracted position to an advanced position. The cartridge body defines a plurality of staple receiving slots and each of the staple receiving slots receives one of the staples. The pusher includes a base member and a plurality of fingers. Each of the plurality of fingers extends distally from the base member into one of the staple receiving slots and has a distal portion that supports one of the staples. The pusher is movable within the cartridge body from a retracted position towards an advanced position to eject the staples from the staple receiving slots. The distal portions of the plurality of fingers are aligned along an axis "P1" and the anvil shaft defines an axis "P2". The axis "P1" defines an angle of from about 2 degrees to about 10 degrees with the axis "P2" when the pusher is in a retracted position, and the axis "P1" is substantially parallel to the axis "P2" when the staples are ejected into the anvil plate.

Other aspects of the disclosure are directed to an end effector including a frame, an anvil plate, and a cartridge assembly. The frame has a U-shaped configuration and includes a first transverse portion, a second transverse portion, and a longitudinal portion interconnecting the first transverse portion and the second transverse portion. The longitudinal portion defines a longitudinal axis. The first transverse portion is spaced from the second transverse portion to define a recess. The first transverse portion of the frame is supported in cantilevered fashion on the longitudinal portion and has a first end coupled to the longitudinal portion of the frame and a second end spaced from the longitudinal portion. The anvil plate is supported on the first transverse portion of the frame and defines an axis that is substantially perpendicular to the longitudinal axis of the longitudinal portion of the frame. The cartridge assembly is supported in the recess defined between the first and second transverse portions of the frame. The cartridge assembly is movable in relation to the anvil plate between spaced and clamped positions. The cartridge assembly includes a cartridge body, staples, and a pusher that is movable within the cartridge body from a retracted position to an advanced position. The cartridge body defines a plurality of staple receiving slots, and each of the staple receiving slots receives one of the staples. The pusher includes a base member and a plurality of fingers. Each of the plurality of fingers extends distally from the base member into one of the staple receiving slots and has a distal portion that supports one of the staples. The pusher is movable within the cartridge body from a retracted position towards an advanced position to eject the staples from the staple receiving slots. When the pusher is in a retracted position, the plurality of staples is spaced from the anvil plate a distance that changes along the longitudinal axis of the anvil plate. In aspects of the disclosure, the base member of the pusher defines a longitudinal axis that is transverse to the longitudinal axis of the longitudinal portion of the frame, and the plurality of fingers each define a longitudinal axis that defines an angle β with the longitudinal axis of the longitudinal portion.

In some aspects of the disclosure, the angle β is from about 78 degrees to about 88 degrees.

In certain aspects of the disclosure, the angle β is about 84 degrees.

In aspects of the disclosure, each of the plurality of fingers of the pusher has the same length.

In some aspects of the disclosure, each staple receiving slot of the plurality of staple receiving slots defines a longitudinal axis that is substantially parallel to the longitudinal axis of the longitudinal portion of the frame.

In certain aspects of the disclosure, the cartridge assembly includes a knife assembly that includes a knife holder and a knife blade.

In aspects of the disclosure, the pusher and the cartridge body define knife slots that receive the knife blade.

In some aspects of the disclosure, when the pusher is in a retracted position, the plurality of staples is spaced from the anvil plate a distance that changes along the longitudinal axis of the anvil plate.

In certain aspects of the disclosure, the distance between the plurality of staples and the anvil plate increases progressively from the second end of the anvil plate towards the first end of the anvil plate such that the staples sequentially engage the anvil plate when the pusher moves from the retracted position towards the advanced position.

Other features of the disclosure will be appreciated from the following description.

BRIEF DESCRIPTION OF THE DRAWINGS

Various aspects of the disclosure are described herein below with reference to the drawings, wherein.

DETAILED DESCRIPTION

Figure 1:
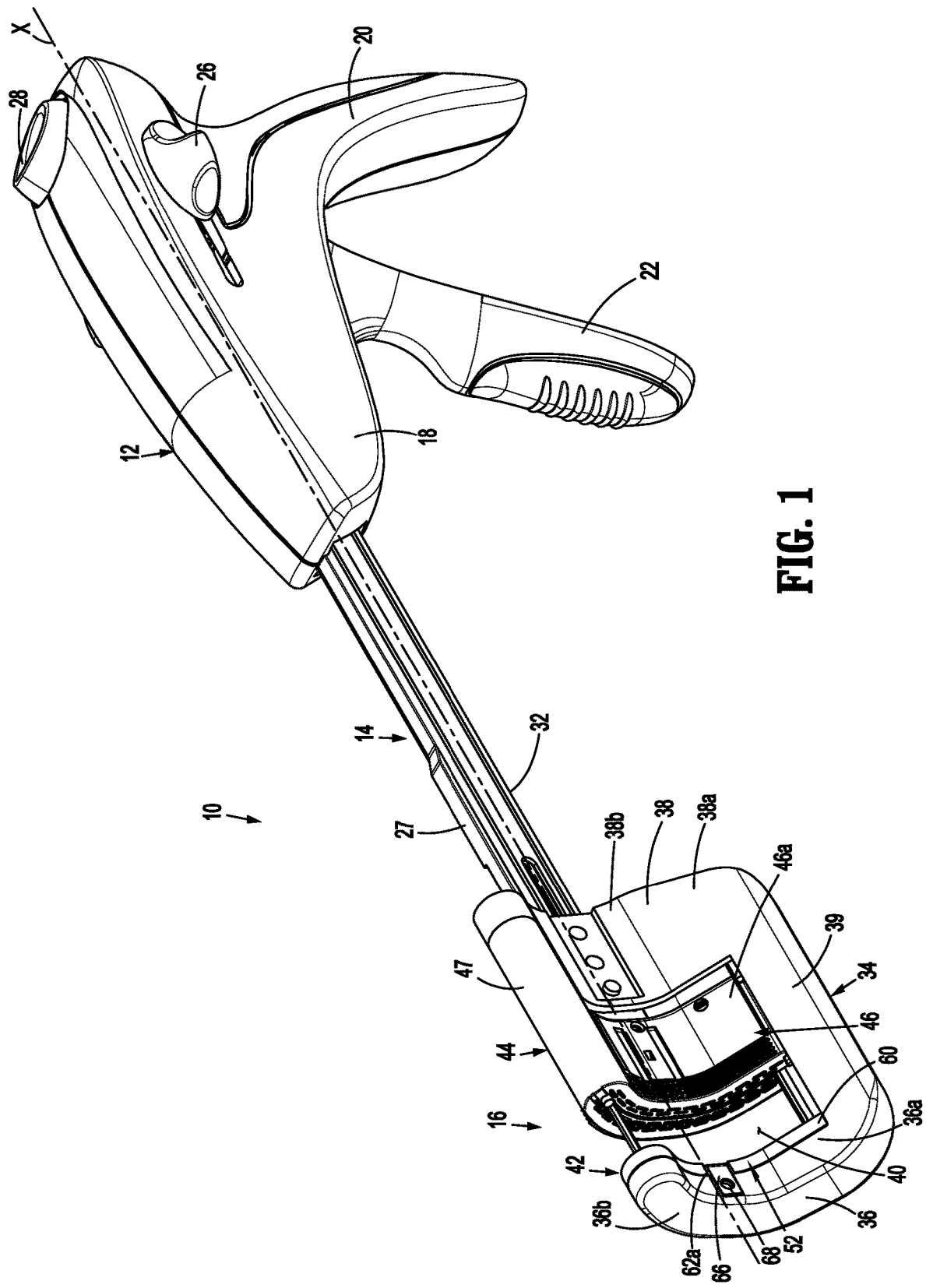
FIG. 1 is a side perspective view of a surgical stapling device according to aspects of the disclosure with an end effector in an open position.

The disclosed surgical stapling devices will now be described in detail with reference to the drawings in which like reference numerals designate identical or corresponding elements in each of the several views. However, it is to be understood that the aspects of the disclosure are merely exemplary and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician during use of the device in its customary manner, while the term "distal" is used generally to refer to that portion of the device that is farther from the clinician during use of the device in its customary manner. In addition, the term "clinician" is used generally to refer to medical personnel including doctors, nurses, and support personnel. "About" or "approximately" or "substantially" as used herein may be inclusive of the stated value and means within an acceptable range of variation for a particular value as determined by one of ordinary skill in the art, considering the measurement in question and the error associated with measurement of the particular quantity (e.g., the limitations of the measurement system). For example, "about" may mean within one or more standard variations, within ±10% of the stated value, or within 2-3 degrees of the stated angle.

FIG. 1 illustrates the disclosed surgical stapling device shown generally as stapling device 10. The stapling device 10 includes a handle assembly 12, an elongate body 14 that extends distally from the handle assembly 12, and an end effector 16 that is supported on a distal portion of the elongate body 14. The elongate body 14 defines a longitudinal axis "X". The handle assembly 12 includes a housing 18 that defines a stationary handle 20 and supports a movable trigger 22. In aspects of the disclosure, the movable trigger 22 is supported by the housing 18 to pivot towards the stationary handle 20 between non-actuated and actuated positions to operate the end effector 16. The handle assembly 12 also supports buttons 26 (only one is shown) that are positioned on each side of the housing 18 and are movable along the housing 18 to advance and retract an alignment pin pusher 27. The alignment pin pusher 27 is positioned and configured to engage an alignment pin (not shown) within the end effector 16 to move the alignment pin between retracted position and advanced positions. The handle assembly 12 also includes a release button 28 that can be depressed to move the end effector 16 from a clamped position to an unclamped position. For a more detailed description of a suitable handle assembly 12, see, e.g., U.S. Pat. No. 6,817,508 ("the '508 patent").

The stapling device 10 includes a frame 32 that extends from the handle assembly 12 to the end effector 16. The frame 32 includes a distal frame portion 34 that has a U-shaped configuration that forms a portion of the end effector 16. The distal frame portion 34 (FIG. 3) has a first transverse portion 36, a second transverse portion 38, and a longitudinal portion 39 that interconnects the first transverse portion 36 and the second transverse portion 38. The first and second transverse portions 36 and 38 are spaced from each other to define a recess 40 that extends between the first and second transverse portions 36 and 38. In some aspects of the disclosure, the first and second transverse portions 36 and 38 are curved along axes transverse to the longitudinal axis "X" of the elongate body 14 of the stapling device 10. Alternately, the first and second transverse portions may be linear or comprised of a plurality of linear portions that are positioned at angles in relation to each other. Each of the first and second transverse portions 36 and 38 has a first end 36a and 38a, respectively, that are coupled to (e.g., formed with) the longitudinal portion 39 of the distal frame portion 34 and a second end 36b and 38b, respectively. The second end 38b of the second transverse portion 38 is coupled to the frame 32 of the elongate body 14. The second end 36b of the first transverse portion 36 of the distal frame portion 34 is spaced from the longitudinal portion 39 such that the first transverse portion 36 is supported on the longitudinal portion 39 in cantilevered fashion.

The end effector 16 includes an anvil assembly 42 and a cartridge assembly 44. The cartridge assembly 44 is removably supported on a clamp slide assembly 46 of the stapling device 10 and includes a body 47 that supports a plurality of staples (not shown). The clamp slide assembly 46 includes a distal portion 46a that is configured to releasably support the cartridge assembly 44. The distal portion 46a is positioned in the recess 40 and is movable between retracted and advanced positions to move the cartridge assembly 44 in relation to the anvil assembly 42 through the recess 40 between an unclamped position (FIG. 1) located adjacent to the second transverse portion 38 of the distal frame portion 34 and a clamped position (FIG. 5) located adjacent the first transverse portion 36 of the distal frame portion 34. For a detailed description of exemplary aspects of the operation and construction of a clamp slide assembly, see the '508 patent.

Figure 5:
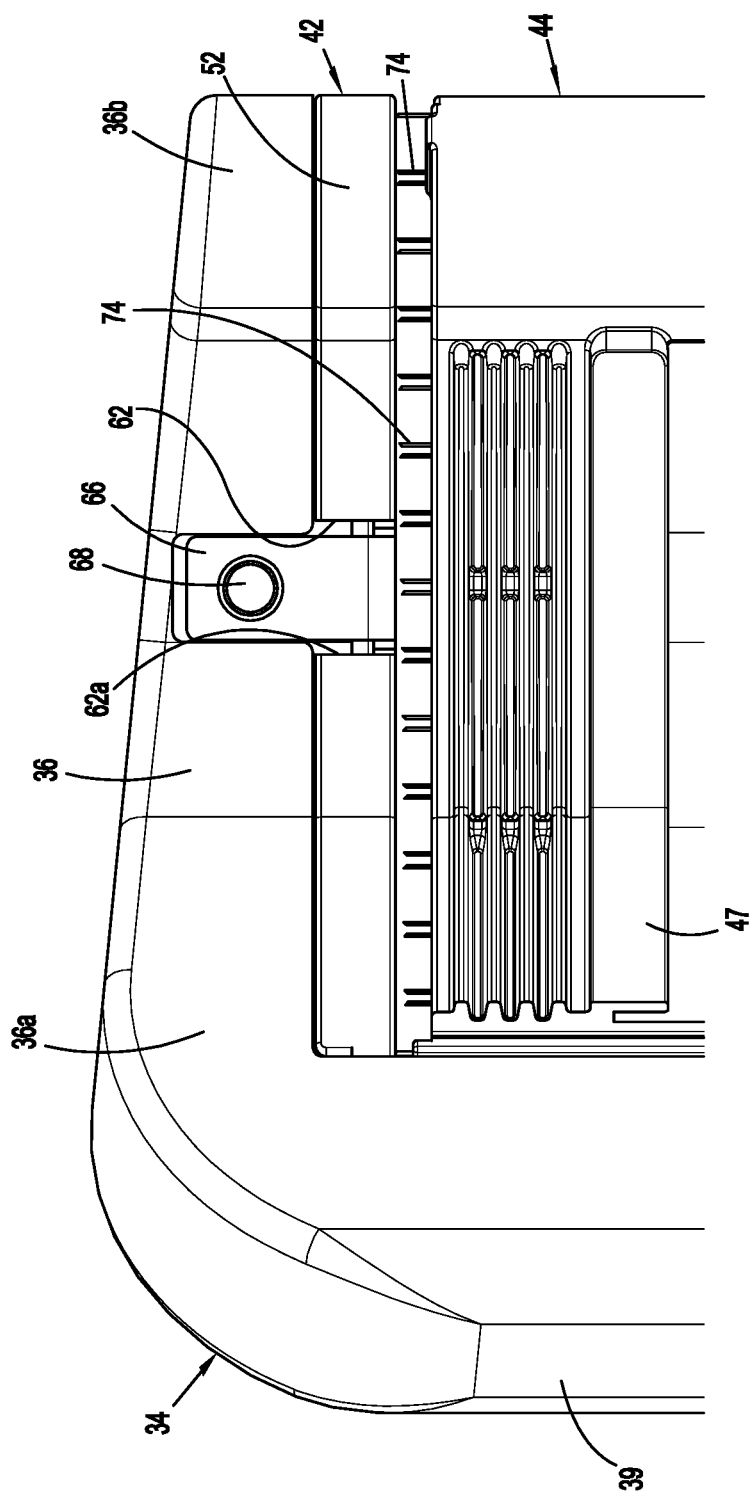
FIG. 5 is a side perspective view of a distal portion of the end effector of the surgical stapling device shown in FIG. 1 as the surgical stapling device begins to be fired and a plurality of staples are ejected from the cartridge assembly towards an anvil assembly of the end effector of the surgical stapling device.
Figure 5A:
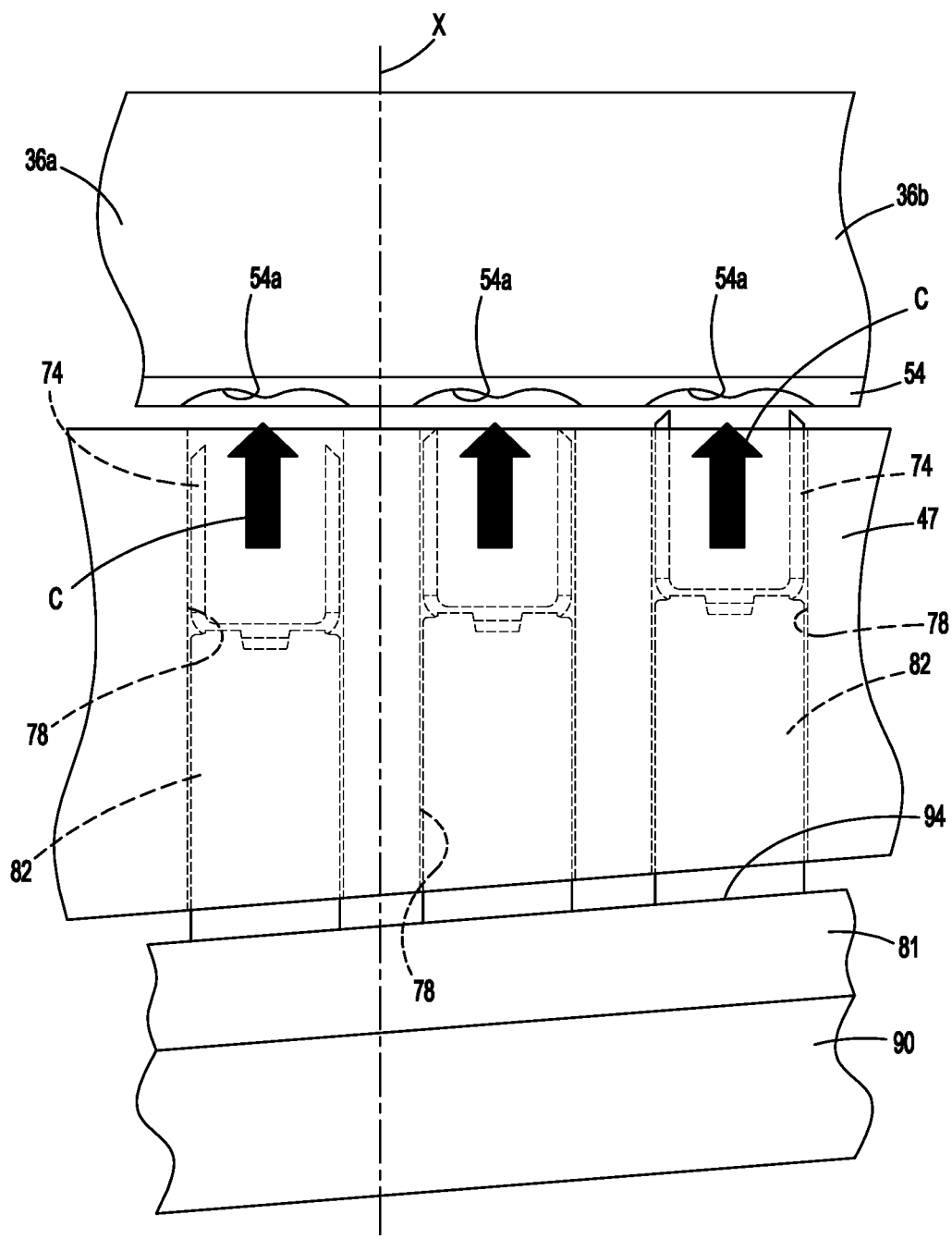
FIG. 5A is a schematic cutaway view of the end effector of the surgical stapling device shown in FIG. 1 as the surgical stapling device is fired before the staples engage the anvil assembly.

The anvil assembly 42 is supported on the first transverse portion 36 of the distal frame portion 34 and includes a cutting plate 52 and an anvil plate 54 (FIG. 5A) that defines a plurality of staple receiving deformations 54a (FIG. 5A). The cutting plate 52 and the anvil plate 54 have configurations that correspond to the configuration of the first transverse portion 36 of the distal frame portion 34. The cutting plate 52 defines opposed cutouts 62a. The anvil plate 54 of the anvil assembly 42 includes flanges 66 that extend through the cutouts 62a of the cutting plate 52 and are secured to the first transverse portion 36 with rivets or pins 68 to secure the anvil plate 54 and the cutting plate 52 to the first transverse portion 36 of the distal frame portion 34 with the cutting plate 52 sandwiched between the first transverse portion 36 of the distal frame portion 34 and the anvil plate 54 (FIG. 5A).

Figure 2:
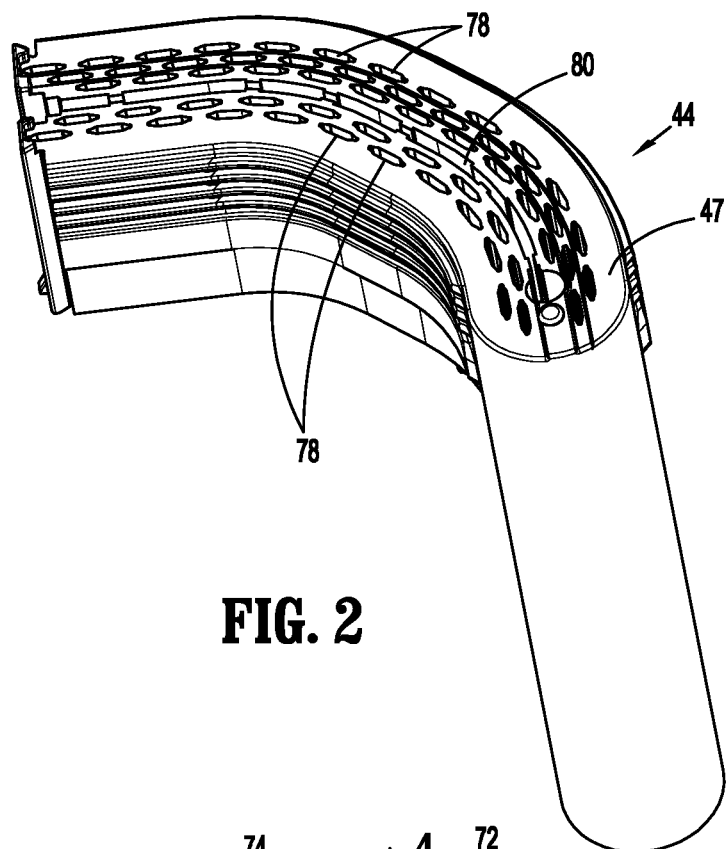
FIG. 2 is a side perspective view from the distal end of a cartridge assembly of the surgical stapling device shown in FIG. 1.
Figure 3:
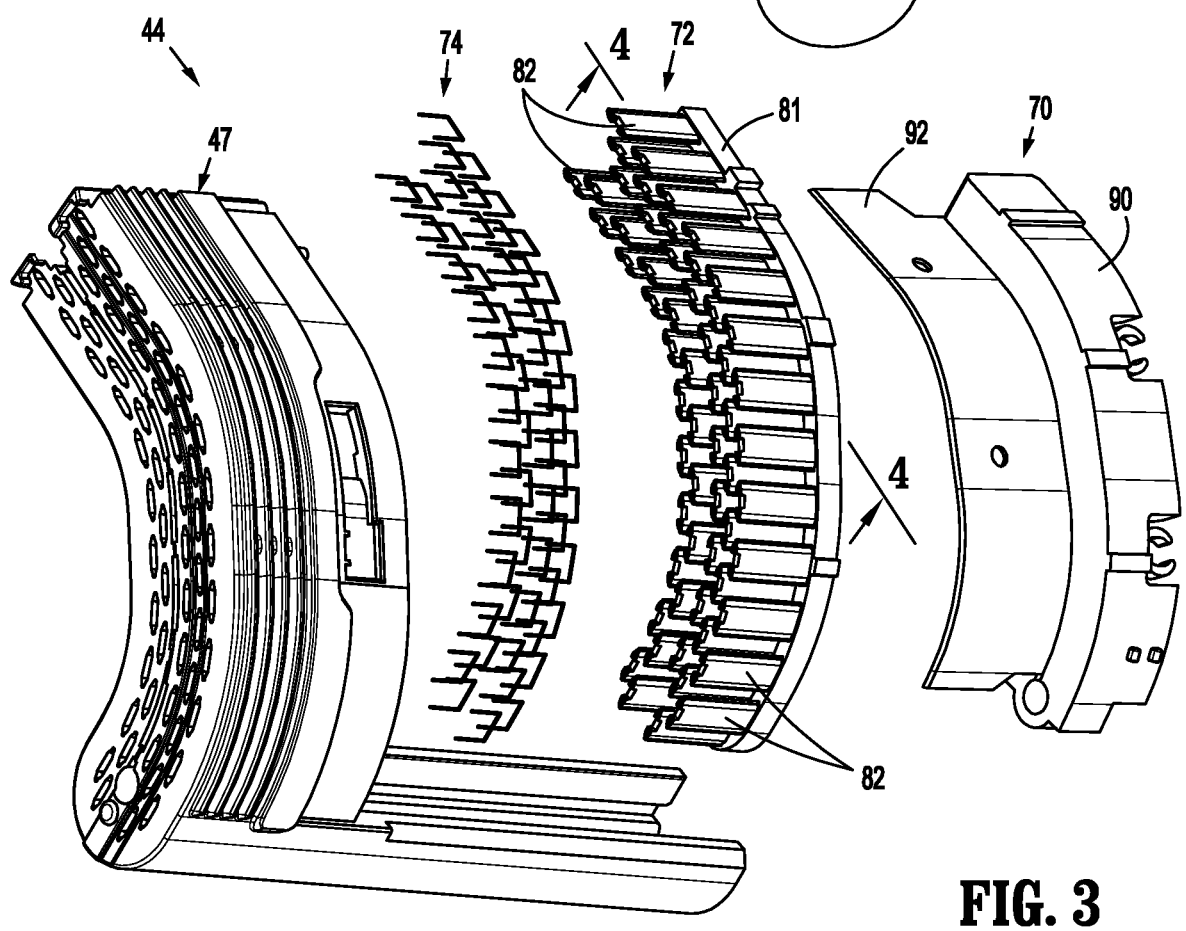
FIG. 3 is an exploded perspective view of the cartridge assembly shown in FIG. 2.

FIGS. 2 and 3 illustrate the cartridge assembly 44 which includes the cartridge body 47, a knife assembly 70, a pusher 72, and staples 74. The cartridge body 47 defines a cavity (not shown) that receives the knife assembly 70 and the pusher 72 such that the knife assembly 70 and the pusher 72 can move within the body 47 of the cartridge assembly 44 from a retracted position to an advanced position. The cartridge body 47 defines a plurality of staple receiving slots 78 (FIG. 2) and a knife slot 80 that extends between the staple receiving slots 78. In aspects of the disclosure, the staple receiving slots 78 are aligned in curved rows on opposite sides of the knife slot 80, and the knife slot 80 is curved and centrally located in the cartridge body 47. It is envisioned that although the cartridge body 47 is shown to have two rows of staple receiving slots 78 on each side of the knife slot 80, one or more rows of staple receiving slots 78 can be provided on each side of the knife slot 80, and the number of rows of staple receiving slots 80 on each side of the knife slot 80 need not be the same. For example, two rows of staple receiving slots 78 can be formed on one side of the knife slot 80 and three rows of staple receiving slots 80 can be formed on the other side of the knife slot 80.

Each of the staples 74 is received in one of the staple receiving slots 78 in the cartridge body 47. The pusher 72 includes a base member 81 and a plurality of pusher fingers 82 that extend distally from the base member 81. Each of the plurality of fingers 82 extends into one of the plurality of staple receiving slots 78 of the cartridge body 47 and includes a distal surface 82a that supports one of the staples 74 within the respective staple receiving slot 78. The base member 81 of the pusher 72 defines a central knife slot (not shown) that is positioned between the rows of the fingers 82 and is aligned with the knife slot 80 in the cartridge body 47.

The knife assembly 70 includes a knife holder 90 and a knife blade 92 that is secured to and extends distally from the knife holder 90. When the cartridge assembly 44 is assembled and the knife assembly 70 is in its retracted position, the knife blade 92 extends from the knife holder 90 through the central knife slot (not shown) in the base member 81 of the pusher 72 and is recessed within the knife slot 80 in the cartridge body 47.

Figure 4:
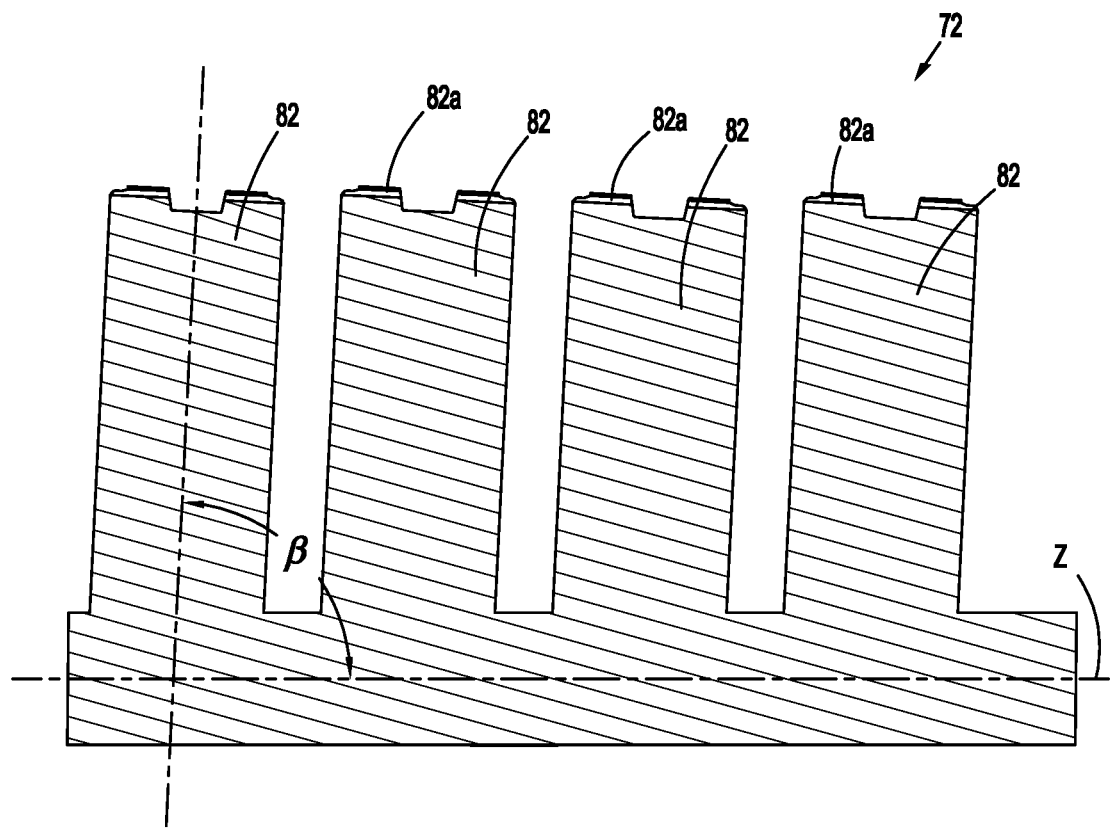
FIG. 4 is a cross-sectional view taken along section line 4-4 of FIG. 3.

FIG. 4 illustrates the pusher 72 of the cartridge assembly 44. As summarized above, the pusher 72 includes a base member 81 and a plurality of fingers 82. The base member 81 defines a longitudinal axis "Z" that extends in a direction transverse to the longitudinal axis "X" of the elongate body 14 (FIG. 1). Each of the plurality of fingers 82 has substantially the same length and extends distally from the base member 81. Each of the plurality of fingers defines a longitudinal axis "Y" that defines an angle β with the longitudinal axis "Z" of the base member 81. In aspects of the disclosure, angle β is from about 78 degrees to about 88 degrees. In some aspects of the disclosure, angle β is about 84 degrees. In aspects of the disclosure, the base member 81 and the plurality of fingers 82 are integrally formed such as by molding. Alternately, the fingers 82 could be form separately from the base member 81 and secured to the base member 81 using any known fastening technique or device.

FIGS. 5 and 5A illustrate the end effector 16 of the stapling device 10 in a clamped position as the stapling device 10 is fired. In this position, the pusher 72 is positioned within the cartridge body 47 with the fingers 82 of the pusher 72 received within the staple receiving slots 78 (FIG. 5A) of the cartridge body 47. As illustrated in FIG. 5A, the staple receiving slots 78 in the cartridge body 47 have axes that are substantially parallel to the longitudinal axis "X" of the elongate body 14 (FIG. 1) of the stapling device 10. As such, when the fingers 82 of the pusher 72 are received in the staple receiving slots 78 of the cartridge body 47, the base member 81 of the pusher 72 from which the fingers 82 extend is angled in relation to the anvil plate 54. The longitudinal axes defined by the fingers 82 of the pusher 72 are substantially parallel to the longitudinal axis "X" of the elongate body 14 (FIG. 1). In this orientation of the pusher 72, the fingers 82 nearer the second end 36b of the first transverse portion 36 of the distal frame portion 34 are closer to the anvil plate 54 than the fingers 82 of the pusher 72 nearer the first end 36a of the first transverse portion 36 of the distal frame portion 34. In aspects of the disclosure, prior to firing of the stapling device 10 (FIG. 1), the fingers 32 of the pusher 72 and the staples 74 supported on the fingers 82 are positioned closest to the anvil plate 54 adjacent the second end 36b of the first transverse portion 36 of the distal frame portion 34 and become progressively further away from the anvil plate 54 towards the first end 36a of the first transverse portion 36 of the distal frame portion 34. In some aspects of the disclosure, a distal portion of the fingers 82 of the pusher 72 extend along an axis "P1" that is substantially parallel to the longitudinal axis "Z" (FIG. 4) of the base member 81 of the pusher 72 and defines the angle β with the longitudinal axes of the fingers 82.

When the cantilevered first transverse portion 36 of the distal frame portion 34 is in a non-deformed position prior to firing of the staples 74 into the anvil plate 54, an axis "P2" (FIG. 5) defined by the anvil plate 54 (which is substantially perpendicular to the longitudinal axis "X" of the elongate body 14) defines angle Q with the axis "P1" defined by the distal portion of the fingers 82. In aspects of the disclosure, the angle Q is from about 2 degrees to about 10 degrees, and in some aspects of the disclosure, about 6 degrees. The relative orientations of the axis "P2" (FIG. 5) defined by the anvil plate 54 and the axis "P1" defined by the distal portions of the fingers 82 of the pusher 72 is provided to compensate for deflection of the first transverse portion 36 of the distal frame portion 34 during firing of the stapling device 10 and to provide a more uniform staple formation along the length of the anvil plate 54.

Each of the staples 74 have a uniform length. Thus, as illustrated in FIG. 5A, when the end effector 16 (FIG. 1) is in a clamped position, prior to firing of the stapling device 10 (FIG. 1), the staples 74 nearest the second end 36b of the first transverse portion 36 of the distal frame portion 34 are spaced more closely to the anvil plate 54 than are the staples 74 positioned nearer the first end 36a of the distal frame portion 34.

Figure 6:
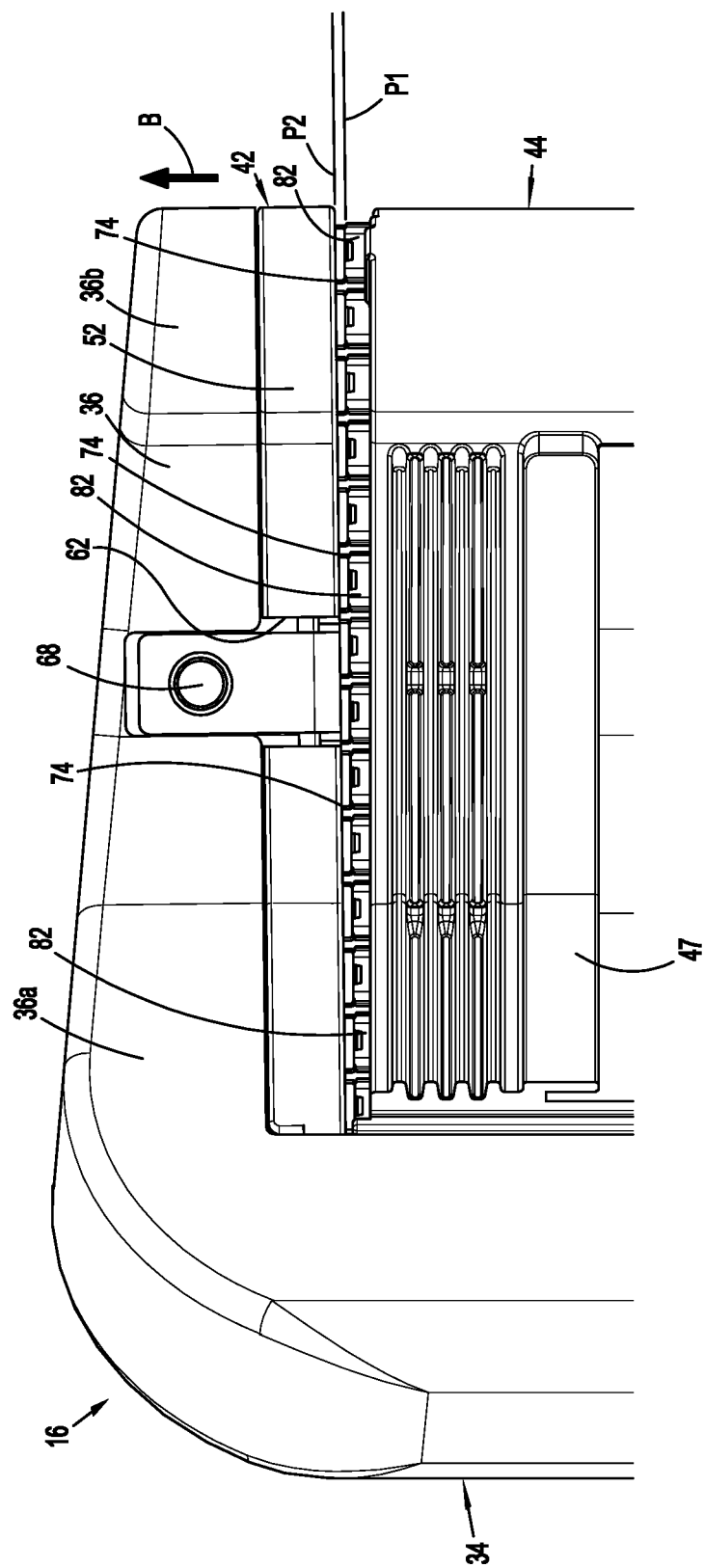
FIG. 6 is a side perspective view of the distal portion of the end effector of the surgical stapling device shown in FIG. 5 after the surgical stapling device has been fired.

FIG. 6 illustrates the end effector 16 of the stapling device 10 as the stapling device 10 is fired to eject staples into the anvil plate 54. When the stapling device 10 is fired to eject the staples 74 from the cartridge body 47 of the cartridge assembly 44, the pusher 72 is advanced in the direction of arrows "C" in FIG. 5A to advance the fingers 82 within the staple receiving slots 78 of the cartridge body 47. As shown, the staples 74 nearer the second end 36b of the first transverse portion 36 of the distal frame portion 34 engage and begin to deform against the anvil plate 54 before the staples 74 located closer to the second end 36b of the first transverse portion 36 of the distal frame portion 34. As such, as the pusher 72 is advanced towards the anvil plate 54, the staples 74 will sequentially engage the anvil plate 54 beginning with the staples 74 nearer the second end 36b of the first transverse portion 36 of the distal frame portion 34 and ending with the staples 74 nearer the first end 36b of the first transverse portion 36 of the distal frame portion 34. Because all the staples do not engage the anvil plate 54 simultaneously, the force required to fire the stapling device 10 is minimized.

When the staples 74 and knife blade 92 (FIG. 3) are driven into the anvil plate 54, a force in a distal direction is applied to the anvil plate 54 which causes the first transverse portion 36 of the distal frame portion 34 to deflect outwardly in the direction of arrow "B" in FIG. 6. Since the first transverse portion 36 of the distal frame portion 34 is supported in cantilevered fashion to the longitudinal portion 39 of the distal frame portion 34, the second end 36b of the first transverse portion 36 of the distal frame portion 34 will deflect outwardly from the cartridge assembly 44 a greater distance than the first end 36a of the distal frame portion 34. This deflection will move the axis "P2" defined by the anvil plate 54 into substantially parallel alignment with the axis "P1" defined by the distal portion of the fingers 82 of the pusher 72. In this position, the gap between the distal portion of the fingers 82 of the pusher 72 and the anvil plate 54 will be substantially uniform along the length of the anvil plate 54 such that the staples 74 will be formed uniformly along the length of the anvil plate 54.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. An end effector comprising:
a frame having a U-shaped configuration and including a first transverse portion, a second transverse portion, and a longitudinal portion interconnecting the first transverse portion and the second transverse portion, the longitudinal portion defining a longitudinal axis, the first transverse portion being spaced from the second transverse portion to define a recess, the first transverse portion of the frame supported in cantilevered fashion on the longitudinal portion and having a first end coupled to the longitudinal portion of the frame and a second end spaced from the longitudinal portion;
an anvil plate supported on the first transverse portion of the frame, the anvil plate defining an axis that is substantially perpendicular to the longitudinal axis of the longitudinal portion of the frame; and
a cartridge assembly supported in the recess defined between the first and second transverse portions of the frame, the cartridge assembly movable in relation to the anvil plate between spaced and clamped positions, the cartridge assembly including a cartridge body, staples, and a pusher that is movable within the cartridge body from a retracted position to an advanced position, the cartridge body defining a plurality of staple receiving slots, each of the staple receiving slots receiving one of the staples, the pusher including a base member and a plurality of fingers, each of the plurality of fingers extending distally from the base member into one of the staple receiving slots and having a distal portion supporting one of the staples, the pusher being movable within the cartridge body from a retracted position towards an advanced position to eject the staples from the staple receiving slots;
wherein the distal portions of the plurality of fingers are aligned along an axis "P1" and the anvil shaft defines an axis "P2", wherein the axis "P1" defines an angle of from about 2 degrees to about 10 degrees with the axis "P2" when the pusher is in a retracted position, and the axis "P1" is substantially parallel to the axis "P2" when the staples are ejected into the anvil plate.

2. The end effector of claim 1, wherein the base member of the pusher defines a longitudinal axis that is transverse to the longitudinal axis of the longitudinal portion of the frame, and the plurality of fingers each define a longitudinal axis that defines an angle β with the longitudinal axis of the longitudinal portion, wherein the angle β is from about 78 degrees to about 88 degrees.

3. The end effector of claim 2, wherein the angle (3 is about 84 degrees.

4. The end effector of claim 2, wherein each of the plurality of fingers of the pusher has the same length.

5. The end effector of claim 4, wherein each staple receiving slot of the plurality of staple receiving slots defines a longitudinal axis that is substantially parallel to the longitudinal axis of the longitudinal portion of the frame.

6. The end effector of claim 1, wherein the cartridge assembly includes a knife assembly that includes a knife holder and a knife blade.

7. The end effector of claim 6, wherein the pusher and the cartridge body define knife slots that receive the knife blade.

8. The end effector of claim 1, wherein the plurality of staples is spaced from the anvil plate, when the pusher is in a retracted position, a distance that changes along the longitudinal axis of the anvil plate.

9. The end effector of claim 8, wherein the distance between the plurality of staples and the anvil plate increases progressively from the second end of the anvil plate towards the first end of the anvil plate such that the staples sequentially engage the anvil plate when the pusher moves from the retracted position towards the advanced position.

10. A surgical stapling device comprising:
a handle assembly;
an elongate body having a proximal portion coupled to the handle assembly and a distal portion; and
an end effector coupled to the distal portion of the elongate body, the end effector including:
a frame having a U-shaped configuration and including a first transverse portion, a second transverse portion, and a longitudinal portion interconnecting the first transverse portion and the second transverse portion, the longitudinal portion defining a longitudinal axis, the first transverse portion being spaced from the second transverse portion to define a recess, the first transverse portion of the frame supported in cantilevered fashion on the longitudinal portion and having a first end coupled to the longitudinal portion and a second end spaced from the longitudinal portion;
an anvil plate supported on the first transverse portion of the frame, the anvil plate defining an axis that is substantially perpendicular to the longitudinal axis of the longitudinal portion of the frame; and
a cartridge assembly supported in the recess defined between the first and second transverse portions of the frame, the cartridge assembly movable in relation to the anvil plate between spaced and clamped positions, the cartridge assembly including a cartridge body, staples, and a pusher that is movable within the cartridge body from a retracted position to an advanced position, the cartridge body defining a plurality of staple receiving slots, each of the staple receiving slots receiving one of the staples, the pusher including a base member and a plurality of fingers, each of the plurality of fingers extending distally from the base member into one of the staple receiving slots and having a distal portion supporting one of the staples, the pusher being movable within the cartridge body from a retracted position towards an advanced position to eject the staples from the staple receiving slots;
wherein the distal portions of the plurality of fingers are aligned along an axis "P1" and the anvil shaft defines an axis "P2", wherein the axis "P1" defines an angle of from about 2 degrees to about 10 degrees with the axis "P2" when the pusher is in a retracted position, and the axis "P 1" is substantially parallel to the axis "P2" when the staples are ejected into the anvil plate.

11. The surgical stapling device of claim 10, wherein the base member of the pusher defines a longitudinal axis that is transverse to the longitudinal axis of the longitudinal portion of the frame, and the plurality of fingers each define a longitudinal axis that defines an angle β with the longitudinal axis of the longitudinal portion, wherein the angle β is from about 78 degrees to about 88 degrees.

12. The surgical stapling device of claim 11, wherein each of the plurality of fingers of the pusher has the same length.

13. The surgical stapling device of claim 12, wherein each staple receiving slot of the plurality of staple receiving slots defines a longitudinal axis that is substantially parallel to the longitudinal axis of the longitudinal portion of the frame.

14. The surgical stapling device of claim 10, wherein the cartridge assembly includes a knife assembly that includes a knife holder and a knife blade.

15. The surgical stapling device of claim 14, wherein the pusher and the cartridge body define knife slots that receive the knife blade.

16. The surgical stapling device of claim 10, wherein the plurality of staples is spaced from the anvil plate, when the pusher is in a retracted position, a distance that changes along the longitudinal axis of the anvil plate.

17. The surgical stapling device of claim 16, wherein the distance between the plurality of staples and the anvil plate increases progressively from the second end of the anvil plate towards the first end of the anvil plate such that the staples sequentially engage the anvil plate when the pusher moves from the retracted position towards the advanced position.

18. The end effector of claim 16, wherein the distal portions of the plurality of fingers are aligned along an axis "P1" and the anvil shaft defines an axis "P2", wherein the axis "P1" defines an angle of from about 2 degrees to about 10 degrees with the axis "P2" when the pusher is in a retracted position, and the axis "P1" is substantially parallel to the axis "P2" when the staples are ejected into the anvil plate.

19. An end effector comprising:
   a frame having a U-shaped configuration and including a first transverse portion, a second transverse portion, and a longitudinal portion interconnecting the first transverse portion and the second transverse portion, the longitudinal portion defining a longitudinal axis, the first transverse portion being spaced from the second transverse portion to define a recess, the first transverse portion of the frame supported in cantilevered fashion on the longitudinal portion and having a first end coupled to the longitudinal portion of the frame and a second end spaced from the longitudinal portion;
   an anvil plate supported on the first transverse portion of the frame, the anvil plate defining an axis that is substantially perpendicular to the longitudinal axis of the longitudinal portion of the frame; and
   a cartridge assembly supported in the recess defined between the first and second transverse portions of the frame, the cartridge assembly movable in relation to the anvil plate between spaced and clamped positions, the cartridge assembly including a cartridge body, staples, and a pusher that is movable within the cartridge body from a retracted position to an advanced position, the cartridge body defining a plurality of staple receiving slots, each of the staple receiving slots receiving one of the staples, the pusher including a base member and a plurality of fingers, each of the plurality of fingers extending distally from the base member into one of the staple receiving slots and having a distal portion supporting one of the staples, the pusher being movable within the cartridge body from a retracted position towards an advanced position to eject the staples from the staple receiving slots;
   wherein the plurality of staples is spaced from the anvil plate, when the pusher is in a retracted position, a distance that changes along the longitudinal axis of the anvil plate.

20. The end effector of claim 19, wherein the distance between the plurality of staples and the anvil plate increases progressively from the second end of the anvil plate towards the first end of the anvil plate such that the staples sequentially engage the anvil plate when the pusher moves from the retracted position towards the advanced position.

* * * * *